US011742072B2

(12) United States Patent
Ahn

(10) Patent No.: US 11,742,072 B2
(45) Date of Patent: Aug. 29, 2023

(54) MEDICAL IMAGE DIAGNOSIS ASSISTANCE APPARATUS AND METHOD USING PLURALITY OF MEDICAL IMAGE DIAGNOSIS ALGORITHMS FOR ENDOSCOPIC IMAGES

(71) Applicant: INFINITT HEALTHCARE CO., LTD., Seoul (KR)

(72) Inventor: Chung Il Ahn, Seoul (KR)

(73) Assignee: INFINITT HEALTHCARE CO., LTD., Seoul (KR)

(*) Notice: Subject to any disclaimer, the term of this patent is extended or adjusted under 35 U.S.C. 154(b) by 167 days.

(21) Appl. No.: 17/089,202

(22) Filed: Nov. 4, 2020

(65) Prior Publication Data

US 2021/0134442 A1 May 6, 2021

(30) Foreign Application Priority Data

Nov. 5, 2019 (KR) .................. 10-2019-0139885

(51) Int. Cl.
*G16H 30/40* (2018.01)
*G16H 50/20* (2018.01)
*G06T 7/00* (2017.01)

(52) U.S. Cl.
CPC .......... *G16H 30/40* (2018.01); *G06T 7/0012* (2013.01); *G16H 50/20* (2018.01);
(Continued)

(58) Field of Classification Search
CPC ................ G06T 7/0012; G16H 30/40
See application file for complete search history.

(56) References Cited

U.S. PATENT DOCUMENTS 8,581,973 B2 * 11/2013 Inoue .................. G06T 7/0012
348/65
9,514,416 B2 * 12/2016 Lee ..................... G16H 50/70
(Continued)

FOREIGN PATENT DOCUMENTS

CN    102753078 A  * 10/2012  ......... A61B 1/00016
CN    106934799 A  *  7/2017  ........... G06K 9/6267
(Continued)

OTHER PUBLICATIONS

A machine translation of CN-102753078-A (Year: 2012).*
A machine translation of CN-106934799-A (Year: 2017).*
A machine translation of CN-107886503-A (Year: 2018).*

*Primary Examiner* — John Villecco
*Assistant Examiner* — Courtney Joan Nelson
(74) *Attorney, Agent, or Firm* — United One Law Group LLC; Kongsik Kim; Jhongwoo Peck

(57) ABSTRACT

Disclosed are an apparatus and method for assisting the diagnosis of a medical image by an automated system. A computing system includes a memory or database that stores a plurality of medical image diagnosis algorithms each having a medical image diagnosis function. A processor inside the computing system extracts diagnosis requirements for a medical image by analyzing the medical image, selects a plurality of diagnosis application algorithms to be applied to the diagnose of the medical image from among a plurality of medical image diagnosis algorithms based on the diagnosis requirements, and generates display information including diagnosis results for the image frame by applying the plurality of selected diagnosis application algorithms to the image frame.

13 Claims, 6 Drawing Sheets

(52) U.S. Cl.
    CPC ............... *G06T 2207/10068* (2013.01); *G06T 2207/20076* (2013.01); *G06T 2207/30096* (2013.01)

(56) References Cited

U.S. PATENT DOCUMENTS

| | | | |
|---|---|---|---|
| 2009/0131746 A1* | 5/2009 | Seo | G16H 30/20 600/101 |
| 2015/0181185 A1* | 6/2015 | Ikemoto | A61B 1/0684 348/71 |
| 2016/0171708 A1* | 6/2016 | Kim | G06T 7/0012 382/128 |
| 2017/0330319 A1 | 11/2017 | Xu et al. | |
| 2018/0253839 A1 | 9/2018 | Zur | |
| 2019/0156483 A1* | 5/2019 | Kono | G06T 7/11 |

FOREIGN PATENT DOCUMENTS

| | | | | |
|---|---|---|---|---|
| CN | 107886503 A | * | 4/2018 | ......... A61B 1/00009 |
| KR | 10-1811028 B1 | | 12/2017 | |
| KR | 10-1818074 B1 | | 1/2018 | |
| KR | 10-1929752 B1 | | 12/2018 | |
| KR | 10-1938992 B1 | | 1/2019 | |
| WO | 2017-165801 A1 | | 9/2017 | |
| WO | WO-2017165801 A1 | * | 9/2017 | ............. A61B 5/055 |
| WO | 2018-015414 A1 | | 1/2018 | |
| WO | 2018-031919 A1 | | 2/2018 | |
| WO | 2018-060723 A1 | | 4/2018 | |

\* cited by examiner

MEDICAL IMAGE DIAGNOSIS ASSISTANCE APPARATUS AND METHOD USING PLURALITY OF MEDICAL IMAGE DIAGNOSIS ALGORITHMS FOR ENDOSCOPIC IMAGES

CROSS-REFERENCE TO RELATED APPLICATION

This application claims under 35 U.S.C. § 119(a) the benefit of priority to Korean Patent Application No. 10-2019-0139885 filed on Nov. 5, 2019, which is incorporated herein by reference in its entirety.

TECHNICAL FIELD

The present invention relates to an apparatus and method for assisting the diagnosis of a medical image by an automated system. More specifically, the present invention relates to a method for generating evaluation scores for artificial intelligence-based medical image diagnosis algorithms and assisting the diagnosis of a medical image based on the evaluation scores and an apparatus for performing the method.

BACKGROUND ART

Endoscopic diagnosis is a medical practice that is considerably frequently performed for the purpose of regular medical examination. There is a demand for a technology that processes real-time images upon endoscopic diagnosis to preprocess them so that an expert can easily identify a lesion at a medical site. Recently, U.S. Patent Application Publication No. US 2018/0253839 entitled "A System and Method for Detection of Suspicious Tissue Regions in an Endoscopic Procedure" introduced a technology that performed a preprocessing process of removing noise from an image frame(video frame) and performed a noise removal preprocessing process and a computer-aided diagnosis (CAD) process in parallel, thereby providing real-time diagnosis assistance display information.

In this technology, the accuracy and reliability of a CAD module are recognized as significantly important factors.

Technologies for segmenting or detecting objects in an image or classifying objects in an image are used for various purposes in image processing. In a medical image, objects in the image are segmented, detected, and classified based on the brightness or intensity values of the image, in which case each of the objects may be an organ of the human body, or a lesion.

Recently, the introduction of deep learning and a convolutional neural network (CNN) as artificial neural networks into the automation of an image processing process has dramatically improved the performance of an automated image processing process.

However, on the other hand, the insides of recent artificial neural networks, such as deep learning and a CNN, approximate black boxes, and thus there is reluctance for a user to fully accept and adopt them even when acquired results are excellent. In particular, reluctance to artificial neural networks stands out as being more important in the medical imaging field in which human life is dealt with.

Under this background, research into explainable artificial intelligence (X-AI) has been attempted in the Defense Advanced Research and Planning (DARPA) of the U.S., etc. (see https://www.darpa.mil/program/explainable-artificial-intellig-ence). However, no visible results have yet been revealed.

In the medical field, as a technique for segmenting, detecting, classifying and diagnosing lesions having complex shapes, a technique for selectively applying a plurality of segmentation algorithms is disclosed in International Publication No. WO2018/015414 entitled "Method and System for Artificial Intelligence Based Medical Image Segmentation."

In the related art document, a technique of comparing pre-trained segmentation algorithms and selecting at least one of the pre-trained segmentation algorithms is applied to the acquisition of a final result of image segmentation.

However, descriptive information (explanation) about the criteria for the selective application of the segmentation algorithms cannot be derived from the related art document, and thus a problem arises in that it is difficult to increase a clinician's confidence in the clinical usefulness of this segmentation technique.

Moreover, Korean Patent No. 10-1938992 entitled "CAD System and Method for Generating Description of Reason for Diagnosis" introduced a technology that generated feature vectors by concatenating feature information extracted based on a DNN in order to derive ground information for the diagnosis of a lesion. However, in Korean Patent No. 10-1938992, an artificial neural network derives feature information by itself, and no verification is made as to whether or not the extracted feature information is clinically useful information. Accordingly, there is little evidence that humans can recognize the above information as a description of the diagnosis result of artificial neural networks.

A similar problem is still present in a medical image diagnosis process in that it is difficult to have clinical confidence in a process in which an artificial intelligence diagnosis system that operates like a black box generates a result.

SUMMARY OF THE DISCLOSURE

Recently, efforts have been made to improve the performance of image segmentation, object detection, and object classification techniques by applying deep learning-based artificial intelligence techniques. However, in the case of deep learning-based artificial intelligence, the fact that there is a black box that prevents a user from determining whether or not a result provided from an operation accidentally exhibits high performance and whether or not a determination process appropriate for a corresponding task has been performed limits the applicability of the deep learning-based artificial intelligence.

In contrast, the use of rule-based training or learning, which is easy to explain, is limited in that better performance cannot be achieved than deep learning. Accordingly, research into deep learning-based artificial intelligence that can provide descriptive information (explanation) while having improved performance is being actively conducted. In the practical application of image processing using an artificial neural network, descriptive information about the basis of diagnosis and classification is required particularly in the medical imaging field. However, descriptive information cannot be derived from the related art.

Even in the above-described related art document (International Publication No. WO2018/015414), it is not possible to derive descriptive information (explanation) on factors that affect the improvement of final segmentation performance, and there is no way to verify that clinically significant feedback has been actually and appropriately applied to the deep learning system even when a clinician provides the clinically significant feedback.

An object of the present invention is to provide evaluation scores, including confidence and accuracy scores, for a plurality of medical image diagnosis algorithms in a process in which a user diagnoses a medical image, thereby improving the accuracy of a medical image diagnosis result obtained by the user.

An object of the present invention is to provide recommended information as descriptive information in a process in which a user derives a final diagnosis result by using artificial intelligence medical image diagnosis algorithms, and to allow the user to provide information about the clinical usefulness of the medical image diagnosis algorithms as quantified information.

An object of the present invention is to provide the optimized content of artificial intelligence medical image diagnosis results for each real-time image frame(video frame) of an endoscopic image.

An object of the present invention is to provide the optimized content of a plurality of artificial intelligence medical image diagnosis results for each real-time image frame.

An object of the present invention is to generate and provide an optimized combination of a plurality of artificial intelligence medical image diagnosis results as display information for each real-time image frame.

An object of the present invention is to provide an optimized combination of a plurality of artificial intelligence medical image diagnosis results capable of efficiently displaying diagnosis results that are likely to be diagnosed, are likely to be overlooked, or have a high level of risk in a current image frame.

An object of the present invention is to provide a user interface and diagnosis computing system that automatically detect and present diagnosis results that are likely to be diagnosed, are likely to be overlooked, or have a high level of risk in a current image frame, so that medical staff can check and review the diagnosis results in real time during an endoscopy.

According to an aspect of the present invention, there is provided a medical image diagnosis assistance apparatus including a computing system, wherein the computing system includes: a reception interface module; a memory or database; and a processor. The reception interface module is configured to receive a medical image, and the memory or database is configured to store a plurality of medical image diagnosis algorithms each having a medical image diagnosis function.

The processor is configured to extract diagnosis requirements for the medical image by analyzing each image frame(video frame) of the medical image, is further configured to select a plurality of diagnosis application algorithms to be applied to the diagnosis of the image frame from among the plurality of medical image diagnosis algorithms based on the diagnosis requirements, and is further configured to generate display information including diagnosis results for the image frame by applying the plurality of selected diagnosis application algorithms to the image frame.

The processor may be further configured to extract context-based diagnosis requirements corresponding to characteristics of the image frame of the medical image by analyzing the image frame of the medical image. The processor may be further configured to select a plurality of diagnosis application algorithms to be applied to the diagnosis of the image frame based on the context-based diagnosis requirements.

The processor may be further configured to select a combination of the plurality of diagnosis application algorithms based on the context-based diagnosis requirements. The processor may be further configured to generate display information including diagnosis results for the image frame by applying the combination of the plurality of diagnosis application algorithms to the image frame.

The combination of the plurality of diagnosis application algorithms may include: a first diagnosis application algorithm configured to be preferentially recommended for the image frame based on the context-based diagnosis requirements; and a second diagnosis application algorithm configured to be recommended based on a supplemental diagnosis requirement derived from the context substrate diagnosis requirements based on a characteristic of the first diagnosis application algorithm.

The context-based diagnosis requirements may include one or more of a body part of the human body included in the endoscopic image frame, an organ of the human body, a relative position indicated by the endoscopic image frame in the organ of the human body, the probabilities of occurrence of lesions related to the endoscopic image frame, the levels of risk of the lesions related to the endoscopic image frame, the levels of difficulty of identification of the lesions related to the endoscopic image frame, and the types of target lesions.

The display information may include the image frame, the diagnosis results selectively overlaid on the image frame, information about the diagnosis application algorithms having generated the diagnosis results, and evaluation scores for the diagnosis application algorithms.

The processor may be further configured to store the display information in the database with the display information associated with the image frame.

The processor may be further configured to generate external storage data in which the display information is associated with the image frame, and to transmit the external storage data to an external database through a transmission interface module so that the external storage data is stored in the external database.

In this case, the plurality of medical image diagnosis algorithms may be artificial intelligence algorithms each using an artificial neural network, and the processor may generate evaluation scores for the respective diagnosis requirements as descriptive information about each of the plurality of medical image diagnosis algorithms.

According to another aspect of the present invention, there is provided a medical image diagnosis assistance method that is executed by a processor inside a computing system for assisting the diagnosis of a medical image and is also executed based on program instructions loaded into the processor.

The medical image diagnosis assistance method includes: receiving, by a reception interface module, a medical image; extracting, by the processor, diagnosis requirements for the medical image by analyzing each endoscopic image frame of a medical image; selecting, by the processor, a plurality of diagnosis application algorithms to be applied to the diagnosis of the image frame from among a plurality of medical image diagnosis algorithms stored in a memory or database inside the computing system and each having a medical image diagnosis function based on the diagnosis requirements; and generating, by the processor, display information including diagnosis results for the image frame by applying the plurality of selected diagnosis application algorithms to the image frame.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Figure 1:
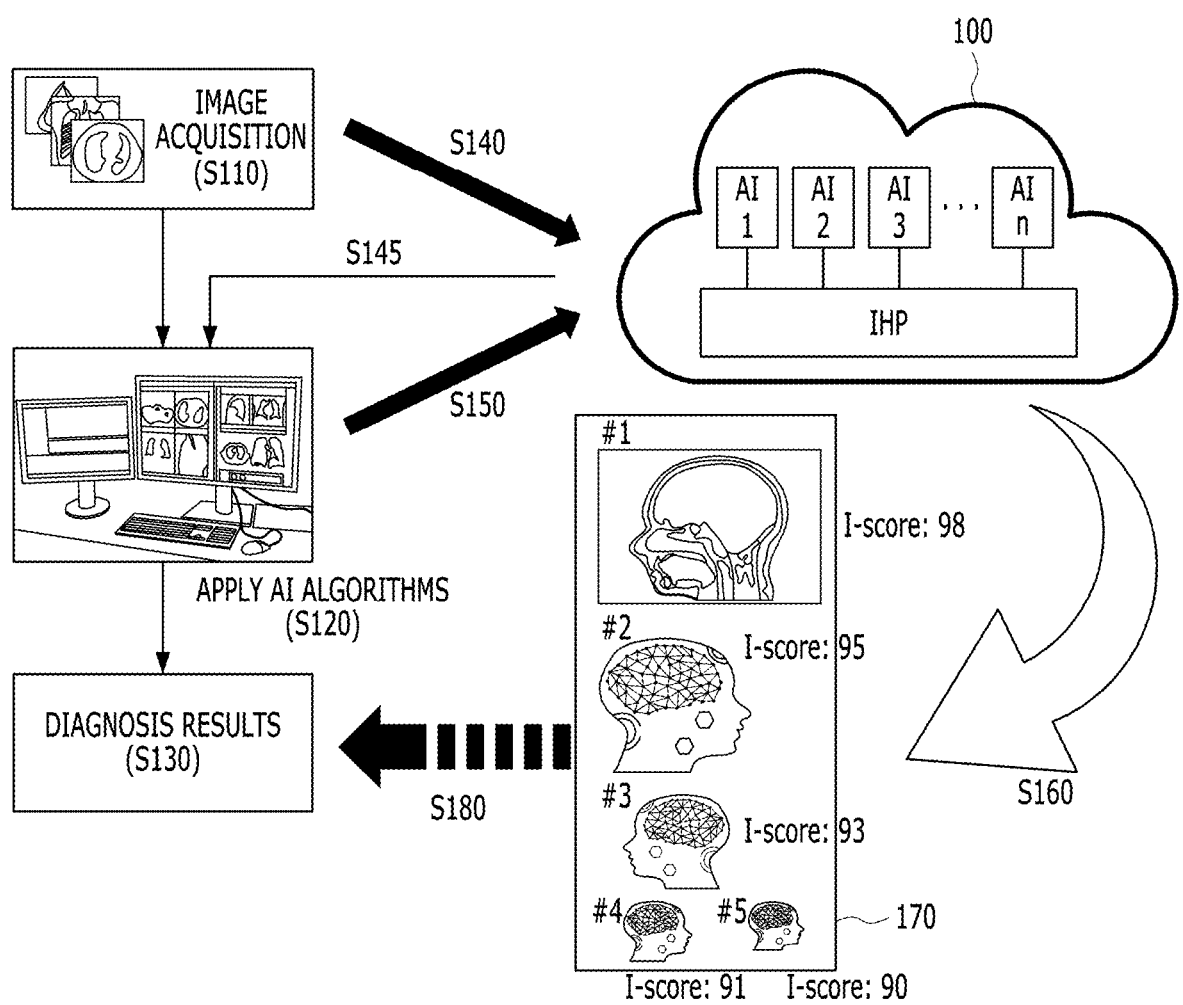
FIG. 1 is a conceptual diagram showing an overall workflow including a medical image diagnosis assistance apparatus according to an embodiment of the present invention.

Embodiments of the present invention will be described in detail below with reference to the accompanying drawings. In the following description, when it is determined that a detailed description of a known component or function may unnecessarily make the gist of the present invention obscure, it will be omitted.

When recently rapidly developed deep learning/CNN-based artificial neural network technology is applied to the imaging field, it may be used to identify visual elements that are difficult to identify with the unaided human eye. The application of this technology is expected to expand to various fields such as security, medical imaging, and non-destructive inspection.

For example, in the medical imaging field, there are cases where cancer tissue is not immediately diagnosed as cancer during a biopsy but is diagnosed as cancer after being tracked and monitored from a pathological point of view. Although it is difficult for the human eye to confirm whether or not corresponding cells are cancer in a medical image, there is an expectation that the artificial neural network technology can provide a more accurate prediction than the human eye.

However, although the artificial neural network technology can yield better prediction/classification/diagnosis results than the human eye in some studies, there is a lack of descriptive information about prediction/classification/diagnosis results acquired through the application of the artificial neural network technology, and thus a problem arises in that it is difficult to accept and adopt the above results in the medical field.

The present invention has been conceived from the intention to improve the performance of the classifying/predicting objects in an image, which are difficult to classify with the unaided human eye, through the application of the artificial neural network technology. Furthermore, even in order to improve the classification/prediction performance of the artificial neural network technology, it is significantly important to acquire descriptive information about the internal operation that reaches the generation of a final diagnosis result based on the classification/prediction processes of the artificial neural network technology.

The present invention may present the performance indicators and clinical usefulness of a plurality of medical image diagnosis algorithms based on artificial neural networks as quantified indicators. As a result, it is possible to provide descriptive information about a process of acquiring a final diagnosis result based on the classification/prediction processes of the artificial neural network, and it is also possible to provide a reference for the determination of whether or not a human user can adopt the classification/prediction/diagnosis results of an artificial neural network.

When the artificial neural networks of the related art are applied to the diagnosis of medical images, they are overfitted only for given tasks, so that statistical accuracy is high but accuracy is low in some clinically important diagnostic points. Many neural networks of the related art are in such a situation, and thus there occur frequent cases where it is difficult for clinicians to have confidence in the diagnosis results for medical images to which the artificial neural networks are applied. This risk is more obvious in that IBM's Watson Solution, a well-known artificial neural network, exhibits a problem in that it is overfitted for patient race information included in learned data and thus it is significantly low in accuracy in the case of the dataset of new race patients.

Therefore, it is significantly important to provide a route through which quantified indicators regarding whether or not clinicians will accept these diagnosis results can be provided and clinicians can provide direct feedback on the generation of the quantified indicators while maximally utilizing the excellent analytical/diagnostic potential of the artificial neural networks.

A medical image diagnosis assistance apparatus and method according to embodiments of the present invention will be described in detail below with reference to FIGS. 1 and 2.

FIG. 1 is a conceptual diagram showing an overall workflow including the medical image diagnosis assistance apparatus according to the embodiment of the present invention. Although the partial sequence (steps S110, S120, and S130) of FIG. 1 may belong to the related art, it is incorporated into the present invention as part of the configuration of the present invention.

Figure 2:
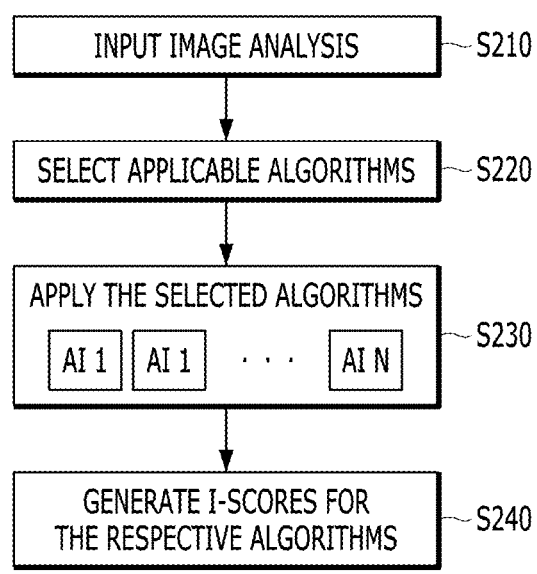
FIG. 2 is an operational flowchart showing a medical image diagnosis assistance method that is performed by the medical image diagnosis assistance apparatus according to an embodiment of the present invention.

FIG. 2 is an operational flowchart showing the medical image diagnosis assistance method that is performed by the medical image diagnosis assistance apparatus according to the embodiment of the present invention.

Referring to FIG. 1, a medical image acquired by a diagnostic imaging apparatus (a modality) at step S110 is transferred to a diagnosis computing terminal of medical staff and is transferred to a computing system 100 according to the present invention at step S140.

The diagnostic imaging apparatus refers to a modality capable of searching for the traces of a lesion within an anatomical structure of the human body or an organ of the human body, such as a CT scanner, an MRI scanner or an ultrasonic diagnosis apparatus, and is not limited to a specific type of apparatus.

The medical image diagnosis assistance apparatus according to the present invention is configured to include the computing system 100, and the medical image diagnosis assistance method according to the present invention is performed by the computing system 100. The computing system 100 includes a memory or database, and also includes a processor. The medical image diagnosis assistance method according to the present invention may be implemented in a form in which program instructions stored in the memory or database are invoked by a processor, loaded into the processor, and executed by the processor.

Referring to FIGS. 1 and 2, the computing system 100 selects a plurality of diagnosis application algorithms to be applied to the diagnosis of an input medical image at step S220 by analyzing the input medical image at step S210.

The computing system 100 generates I-scores 170 for the plurality of respective diagnosis application algorithms as evaluation scores at steps S160 and S240. The computing system 100 may generate a plurality of recommended diagnosis results for one examination or at least one medical image at one time.

The computing system 100 may store a plurality of medical image diagnosis algorithms each having a medical image diagnosis function in the memory or database. The processor of the computing system 100 extracts a diagnosis requirement for the medical image by analyzing the medical image at step S210. The processor selects a plurality of diagnosis application algorithms to be applied to the diagnosis of the medical image from among the plurality of medical image diagnosis algorithms based on the diagnosis requirement at step S220.

When the plurality of selected diagnosis application algorithms is applied to the medical image and a plurality of diagnosis results for the medical image is generated, the processor of the computing system 100 stores the plurality of diagnosis results for the medical image in the memory or database inside the computing system 100 with the plurality of diagnosis results for the medical image associated with the plurality of respective diagnosis application algorithms. In this case, for ease of description, for example, it is assumed that when the plurality of diagnosis application algorithms includes a first diagnosis algorithm and a second diagnosis algorithm, a first diagnosis result based on the first diagnosis algorithm and a second diagnosis result based on the second diagnosis algorithm are obtained.

The processor of the computing system 100 generates I-scores 170 for the plurality of respective diagnosis application algorithms as evaluation scores at steps S160 and S240.

At step S130, diagnosis results are generated using results to which artificial intelligence algorithms are applied by the diagnosis computing terminal of the medical staff at step S120. In this case, the comments of the medical staff may be added at step S130 of generating diagnosis results.

In the medical image diagnosis assistance apparatus according to the present invention, the I-scores 170, i.e., evaluation scores, are transferred from the computing system 100 to the diagnosis computing terminal of the medical staff at step S180. Final diagnosis texts may be generated by incorporating the I-scores 170, i.e., evaluation scores, into the generation of the diagnosis results at step S130. According to an embodiment of the present invention, the computing system 100 may generate diagnosis texts together with the I-scores 170, i.e., evaluation scores, and transfer them to the computing system of the medical staff at step S180. In this case, the diagnosis texts generated by the computing system 100 may be written using the diagnosis results based on diagnosis application algorithms having higher I-scores 170, i.e., higher evaluation scores.

The computing system 100 may provide a user interface configured to display a plurality of recommended diagnosis results at one time, to generate the plurality of recommended diagnosis results without requiring the additional operation of a user, and to check/display the plurality of recommended diagnosis results. The processor of the computing system 100 may generate display information including evaluation scores for the plurality of respective diagnosis application algorithms and the plurality of diagnosis results, and may provide a user with a menu configured to allow a user to select one or more of the plurality of diagnosis application algorithms.

The computing system 100 provides a system or interface configured to display the comparisons between suspected body parts for one examination or at least one image or to present diagnosis texts in response to a search for a plurality of recommended diagnosis results. The processor of the computing system 100 may display a first diagnosis result and a second diagnosis result for suspected lesion locations within the medical image so that they can be compared with each other, and may generate a first diagnosis text based on the first diagnosis result for the suspected lesion locations within the medical image and a second diagnosis text based on the second diagnosis result therefor. In other words, when different diagnosis results are obtained by applying different diagnosis application algorithms to the same medical image, this plurality of diagnosis results is displayed such that they can be compared with each other, and the user may select any one of first and second diagnosis results and generate it as a final diagnosis result. In this case, a user interface configured to determine whether or not the user will accept a diagnosis result for each of the suspected lesion locations presented by the first and second diagnosis results may be provided, and the accuracies of the first and second diagnosis results may be compared with each other for each lesion diagnosis result. Information about whether or not the user finally has accepted each of the plurality of automatic diagnosis results for each lesion diagnosis result may be transferred back to the computing system 100 as feedback information, and may be utilized as sub-information that constitutes part of an evaluation score.

The computing system 100 may provide a user interface configured to compare and display base images or diagnosis texts corresponding to the plurality of recommended diagnosis results. The processor of the computing system 100 generates first diagnosis base image information including information about suspected lesion locations within the medical image associated with the first diagnosis result and second diagnosis base image information including information about suspected lesion locations within the medical image associated with the second diagnosis result, and may generate a first diagnosis text based on the first diagnosis base image information and the first diagnosis result and a second diagnosis text based on the second diagnosis base image information and the second diagnosis result. When the first diagnosis result and the second diagnosis result are different for the same suspected lesion location within the medical image, the user may invoke and compare the first diagnosis base image information of the first diagnosis result and the second diagnosis base image information of the second diagnosis result. Since the originals of the base medical images are the same and the regions diagnosed as lesions by the respective diagnosis application algorithms are different from each other, the regions of the originals of the medical images referred to by the respective diagnosis application algorithms as bases for the diagnoses of the lesions may be different from each other in this case. For example, when the diagnosis application algorithms perform a function such as object detection, diagnosis base image information may be represented as a box including a specific object or information about the contour lines of a specific object. Furthermore, information about the probabilities at which the diagnosis application algorithms have detected the corresponding objects may be included in and generated as diagnosis base image information.

The computing system 100 may provide a user interface configured to allow recommended diagnosis results to be selected using I-scores 170, i.e., internally calculated evaluation scores, and to allow a radiologist to evaluate/check diagnostic confidence in corresponding recommended diagnoses (e.g., recommended diagnosis algorithms consistent with the diagnosis results of the radiologist) because the evaluation scores are also displayed. The processor of the computing system 100 may select the first and second diagnosis results from among the plurality of diagnosis results as recommended diagnosis results based on the evaluation scores. The processor may generate display information including the evaluation score for the first diagnosis algorithm, the first diagnosis result, the evaluation score for the second diagnosis algorithm, and the second diagnosis result.

The computing system 100 may generate an evaluation score based on the confidence score of a corresponding diagnosis algorithm, the accuracy score of the diagnosis algorithm, and the evaluation confidence score of a radiologist who provides feedback. The processor may generate the confidence score of each of the plurality of medical image diagnosis algorithms, the accuracy score of the medical image diagnosis algorithm, and the evaluation confidence score of the medical image diagnosis algorithm by the user as sub-evaluation items based on a corresponding one of the plurality of diagnosis results and feedback on the diagnosis result, and may generate an evaluation score based on the sub-evaluation items.

For example, the criteria for the generation of the evaluation score may be implemented as follows:

$I\text{-score} = a \times (\text{the confidence score of an artificial intelligence algorithm}) + b \times (\text{the accuracy score of the artificial intelligence algorithm}) + c \times (\text{the evaluation confidence score of the artificial intelligence algorithm by a radiologist})$ (1)

The confidence score of the algorithm may be given to the algorithm by the radiologist. In other words, when it is determined that the first diagnosis result is more accurate than the second diagnosis result, a higher confidence score may be given to the first diagnosis result.

The accuracy score of the algorithm may be determined based on the extent to which the radiologist accepts the diagnosis result of the algorithm without a separate score giving process. For example, in the case where when the first diagnosis result presents ten suspected lesion locations, the radiologist approves nine suspected lesion locations, the accuracy score may be given as 90/100.

Another embodiment in which the accuracy score of the algorithm is given may be a case where an accurate result is revealed through a biopsy or the like. In this case, the accuracy of the diagnosis result of the diagnosis algorithm may be revealed in comparison with the accurate result obtained through the biopsy. When the user inputs the accurate result, obtained through the biopsy, to the computing system 100, the computing system 100 may calculate the accuracy score of the diagnosis algorithm by comparing the diagnosis result with the accurate result obtained through the biopsy (a reference).

The evaluation confidence score of the radiologist may be provided as a confidence score for the evaluation of the radiologist. In other words, when the radiologist is an expert having a loner experience in a corresponding clinical field, a higher evaluation confidence score may be given accordingly. The evaluation confidence score may be calculated by taking into consideration the years of experience of the radiologist, the specialty of the radiologist, whether or not the radiologist is a medical specialist, and the experience in the corresponding clinical field.

The computing system 100 may update evaluation score calculation criteria according to a predetermined internal schedule while continuously learning the evaluation score calculation criteria by means of an internal artificial intelligence algorithm. The processor may assign weights to the confidence scores of the plurality of respective medical image diagnosis algorithms, the accuracy scores of the plurality of respective medical image diagnosis algorithms, and the evaluation confidence scores of the plurality of respective medical image diagnosis algorithms by the user, which are sub-evaluation items, and may update the weights of the sub-evaluation items so that the weights of the sub-evaluation items can be adjusted according to a target requirement based on the plurality of diagnosis results and feedback on the plurality of diagnosis results by the user.

An example of the target requirement may be a case where adjustment is performed such that there is a correlation between the confidence of the user in the algorithms and the accuracy of the algorithms. For example, first and second diagnosis algorithms having the same accuracy score may have different confidence scores that are given by a radiologist. In this case, when confidence scores are different from each other while exhibiting a certain tendency after the removal of the general errors of the evaluation of the radiologist, it can be recognized that the confidence of the radiologist in the first diagnosis algorithm is different from the confidence of the radiologist in the second diagnosis algorithm. For example, in the case where the first and second diagnosis algorithms generate accurate diagnosis results at nine of a total of ten suspected lesion locations, resulting in an accuracy score of 90/100 but only the first diagnosis algorithm accurately identifies a severe lesion and the second diagnosis algorithm does not identify the lesion, the confidence of the radiologist in the first diagnosis algorithm may be different from the confidence of the radiologist in the second diagnosis algorithm. A means for adjusting the correlation between the accuracy and the confidence may be a means for adjusting the weights of the respective sub-evaluation items or subdividing criteria for the selection of target lesions related to the determination of accuracy. In this case, there may be used a method that classifies lesions according to criteria such as the hardness/severity of an identified lesion, the position of the lesion from the center of a medical image, and the difficulty of identifying the lesion (the difficulty is high in a region where bones, organs, and blood vessels are mixed in a complicated form) and assigns different weights to the diagnosis accuracies of lesions in respective regions.

The computing system 100 may include a function of automatically allocating a plurality of artificial intelligence algorithms that are applicable depending on an image. To determine a plurality of artificial intelligence algorithms applicable to an image, the computing system 100 may classify one examination or at least one image by means of a separate image classification artificial intelligence algorithm inside a recommendation diagnosis system, and may then apply a plurality of artificial intelligence algorithms.

The processor may extract an image segmentation result for the medical image, a clinical requirement for the medical image, and a diagnosis requirement for the medical image based on information about the examinee of the medical image. The processor may select a plurality of diagnosis application algorithms to be applied to the diagnosis of the medical image based on at least one of suitability for the diagnosis requirement and the evaluation scores for the plurality of respective medical image diagnosis algorithms. In other words, information about a request for the acquisition of the medical image, the details of a suspected disease accompanying the request, the department of the clinician, and a body part or organ photographed in the medical image, which is transferred from the clinician to the radiologist, may be taken into consideration as the clinical requirement. Furthermore, when each of the diagnosis application algorithms is selected, information about the purpose of diagnosis and the object of diagnosis defined by the artificial intelligence algorithm may be taken into consideration, and also the gender and age of the examinee of the medical image and the severity of a disease may be taken into consideration.

The computing system 100 may subdivide the recommended items for the same diagnosis purpose (the same diagnosis requirement) for the same body part while associating an image analysis function and an evaluation score generation function with each other. For example, there may be provided a system capable of recommending an algorithm suitable for the diagnosis of the center of a particular organ, an algorithm suitable for the diagnosis of the periphery of a particular organ, an algorithm suitable for a region where bones, organs, and blood vessels are mixed in a complicated form, etc. in a subdivided manner. This function may be implemented via a separate artificial intelligence algorithm.

The processor may generate detailed evaluation items for each diagnosis requirement, including information about the type of organ, the location of a lesion, and the relative positions of the organ and the lesion for each diagnosis requirement, based on image segmentation and processing results for the medical image, and may generate evaluation scores for the plurality of respective medical image diagnosis algorithms with respect to each of the detailed evaluation items for each diagnosis requirement.

The computing system 100 may subdivide criteria items for the generation of evaluation scores based on image diagnosis results. For example, an algorithm with high overall accuracy and low confidence may exhibit high overall accuracy but may exhibit low accuracy for a specific item. In this case, the computing system 100 may specifically select diagnosis items that highly affect confidence. In other words, the computing system 100 may refine and subdivide the criteria items for the generation of evaluation scores by using the image diagnosis results.

The processor may generate a confidence score for each of the plurality of medical image diagnosis algorithms, an accuracy score for the medical image diagnosis algorithm, and an evaluation confidence score for the medical image diagnosis algorithm by the user as sub-evaluation items based on a corresponding one of the plurality of diagnosis results and feedback on the diagnosis result by the user. The processor may select each of the plurality of diagnosis application algorithms based on the correlation between each detailed evaluation item for the diagnosis requirement and a corresponding one of the sub-evaluation items.

In an embodiment of the present invention, the plurality of medical image diagnosis algorithms may be medical image diagnosis algorithms using artificial neural networks. In this case, the evaluation score and the sub-evaluation items may be generated as descriptive information for each diagnosis algorithm, and the computing system 100 may feed the evaluation score and the sub-evaluation items back to the creator of the diagnosis algorithm so that the information can be used to improve the diagnosis algorithm. In this case, when each of the artificial neural networks is an artificial neural network using a relevance score and a confidence level, which is being studied recently, a statistical analysis is performed with the evaluation score and the sub-evaluation items associated with the relevance score or confidence level of the artificial neural network, and thus the evaluation score and the sub-evaluation items may affect the improvement of the diagnosis algorithm.

In an embodiment of the present invention, after the applicable algorithms have been selected by the computing system 100, information about the selected diagnosis application algorithms may be transferred to the diagnosis computing terminal of the medical staff at step S145, and artificial intelligence algorithms (the diagnosis application algorithms) may be actually applied to the medical image in the diagnosis computing terminal of the medical staff at step S120.

In this case, a plurality of diagnosis results obtained by actually applying the plurality of diagnosis application algorithms is transferred to the computing system 100 at step S150. The computing system 100 may store the plurality of diagnosis results in the memory or database inside the computing system 100 with the plurality of diagnosis results associated with the plurality of diagnosis application algorithms. In this case, the feedback indicators input for the plurality of diagnosis results or the plurality of diagnosis application algorithms via the diagnosis computing terminal of the medical staff by the medical staff may be also fed back to the computing system at step S150. The feedback indicators may be stored in the memory or database inside the computing system 100 in association with the evaluation targets, i.e., the plurality of diagnosis results or the plurality of diagnosis application algorithms.

This embodiment of the present invention is designed to provide advantages obtainable by the present invention while minimizing the deformation of the medical image diagnosis sequence S110, S120 and S130 of the related art as much as possible.

In another embodiment of the present invention, the computing system 100 may perform the process of selecting a plurality of diagnosis application algorithms and generating a plurality of diagnosis results by applying the plurality of diagnosis application algorithms to a medical image by itself. In this case, the computing system 100 may transfer not only information about the selected diagnosis application algorithms but also the plurality of diagnosis results based on the diagnosis application algorithms to the diagnosis computing terminal of the medical staff at step S145, and the results obtained by applying artificial intelligence algorithms (the diagnosis application algorithms) to the medical image may be displayed on the diagnosis computing terminal of the medical staff at step S120.

In this case, an embodiment of the present invention may provide advantages obtainable by present invention even when the computing power of the diagnosis computing terminal of the medical staff is not high, e.g., the diagnosis computing terminal of the medical staff is a mobile device or an old-fashioned computing system. In this case, in an embodiment of the present invention, an agent that applies the artificial intelligence algorithms to the medical image is the computing system 100, the computing system 100 functions as a type of server, and the diagnosis computing terminal of the medical staff may operate based on a thin-client concept. In this case, in an embodiment of the present invention, the feedback indicators input for the plurality of diagnosis results or the plurality of diagnosis application algorithms via the diagnosis computing terminal of the medical staff by the medical staff may be fed back to the computing system at step S150. The feedback indicators may be stored in the memory or database inside the computing system 100 in association with the evaluation targets, i.e., the plurality of diagnosis results or the plurality of diagnosis application algorithms.

As described above, in an embodiment of the present invention, step S230 of applying the selected algorithms may be performed in the diagnosis system of the clinician at step S120, and a plurality of diagnosis results may be transferred to the computing system 100 at step S150. In another embodiment of the present invention, overall step S230 of applying the selected algorithms may be performed within the computing system 100 and then the results of the application may be displayed on the diagnosis system of the clinician at steps S145 and S120.

Figure 3:
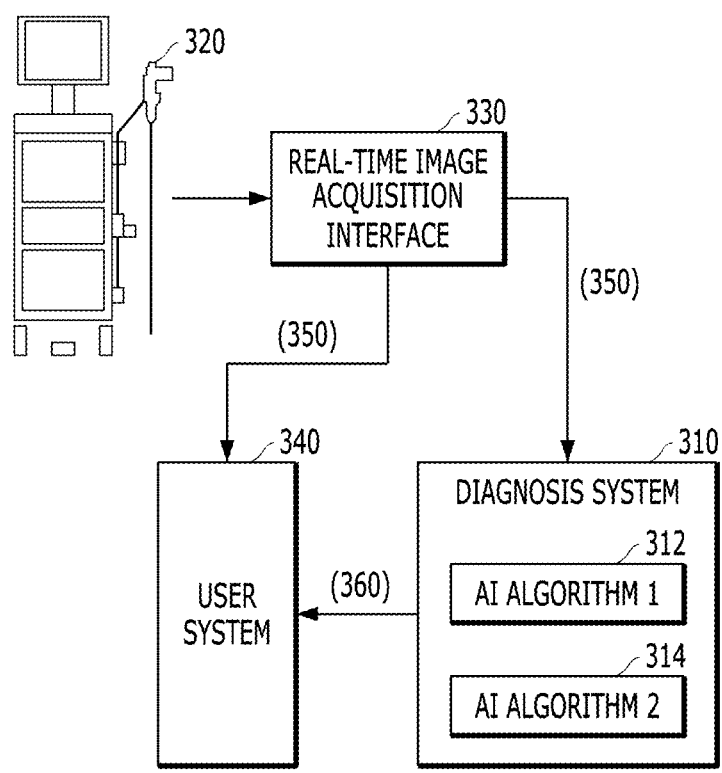
FIG. 3 is a conceptual diagram showing an overall workflow including a medical image diagnosis assistance apparatus according to an embodiment of the present invention.

FIG. 3 is a conceptual diagram showing an overall workflow including a medical image diagnosis assistance apparatus according to an embodiment of the present invention.

A real-time image acquisition interface module 330 acquires a real-time endoscopic image 350 from endoscopy equipment 320. The real-time image acquisition interface module 330 transmits the real-time endoscopic image 350 to a user system 340 and a diagnosis system 310. The diagnosis system 310 includes at least two artificial intelligence algorithms 312 and 314, and generates display information 360 including diagnosis information by applying the at least two artificial intelligence algorithms 312 and 314 to the real-time endoscopic image 350. The diagnosis system 310 transfers the display information 360 to the user system 340, and the user system 340 may overlay the display information 360 on the real-time endoscopic image 350 or display the real-time endoscopic image 350 and the display information 360 together.

Although the embodiment in which the diagnosis system 310 and the user system 340 are separated from each other is illustrated in FIG. 3 for ease of illustration, it will be apparent to those skilled in the art that the diagnosis system 310 and the user system 340 may be implemented in a single system according to another embodiment of the present invention.

Figure 4:
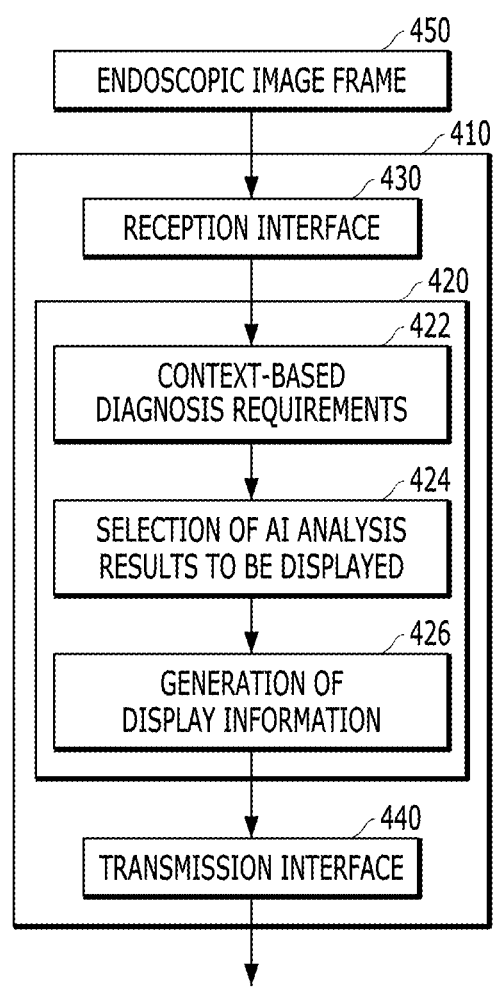
FIG. 4 is a diagram showing the medical image diagnosis assistance apparatus of FIG. 3 in detail.

FIG. 4 is a diagram showing the medical image diagnosis assistance apparatus of FIG. 3 in detail.

The real-time endoscopic image 350 may be divided into individual image frames. In this case, each of the endoscopic image frames 450 may be received or input by a reception interface module 430.

The diagnosis computing system 410 includes the reception interface module 430, a processor 420, and a transmission interface module 440. The processor 420 includes sub-modules the functions of which are internally implemented by hardware or software. The processor 420 may include a first sub-module 422 configured to extract context-based diagnosis requirements, a second sub-module 424 configured to select artificial intelligence analysis results to be displayed from among diagnosis results generated by applying artificial intelligence diagnosis algorithms to the endoscopic image frame 450, and a third sub-module 426 configured to generate the display information 360 to be displayed on the screen of the user system 340.

The plurality of artificial intelligence diagnosis algorithms is stored in memory or database (not shown) inside the diagnosis computing system 410, is applied to the endoscopic image frame 450 under the control of the processor 420, and generates diagnosis results for the endoscopic image frame 450.

Although a case where the plurality of artificial intelligence diagnosis algorithms is stored in the memory or database (not shown) inside the diagnosis computing system 410 and run under the control of the processor 420 is described in the embodiment of FIG. 4, the plurality of artificial intelligence diagnosis algorithms may be stored in a memory or database (not shown) outside the diagnosis computing system 410 according to another embodiment of the present invention. When the plurality of artificial intelligence diagnosis algorithms is stored in the memory or database (not shown) outside the diagnosis computing system 410, the processor 420 may control the memory or database (not shown) outside the diagnosis computing system 410 via the transmission interface module 440 so that the plurality of artificial intelligence diagnosis algorithms is applied to the endoscopic image frame 450 and diagnosis results for the endoscopic image frame 450 are generated. In this case, the generated diagnosis results may be transferred to the diagnosis computing system 410 through the reception interface module 430, and the processor 420 may generate the display information 360 based on the diagnosis results.

The processor 420 extracts diagnosis requirements for the endoscopic image frame 450 by analyzing the endoscopic image frame 450, which is an image frame (video frame) of a medical image. The processor 420 selects a plurality of diagnosis application algorithms to be applied to the diagnosis of the endoscopic image frame 450 from among the plurality of medical image diagnosis algorithms based on the diagnosis requirements, and the processor 420 generates the display information 360 including diagnosis results for the endoscopic image frame 450 by applying the plurality of diagnosis application algorithms to the endoscopic image frame 450. This process is performed on each of the endoscopic image frames 450 by the processor 420.

The processor 420 may extract context-based diagnosis requirements corresponding to the characteristics of the endoscopic image frame 450 by analyzing the endoscopic image frame 450. The processor 420 may select a plurality of diagnosis application algorithms to be applied to the diagnosis of the endoscopic image frame 450 based on the context-based diagnosis requirements.

The processor 420 may select a combination of a plurality of diagnosis application algorithms based on the context-based diagnosis requirements. The processor 420 may generate the display information 360 including diagnosis results for the endoscopic image frame 450 by applying the plurality of diagnosis application algorithms to the endoscopic image frame 450.

The combination of a plurality of diagnosis application algorithms may include a first diagnosis application algorithm configured to be preferentially recommended for the endoscopic image frame 450 based on context-based diagnosis requirements, and a second diagnosis application algorithm configured to be recommended based on a supplemental diagnosis requirement derived from the context substrate diagnosis requirements based on a characteristic of the first diagnosis application algorithm.

The context-based diagnosis requirements may include one or more of a body part of the human body included in the endoscopic image frame 450, an organ of the human body, a relative position indicated by the endoscopic image frame 450 in the organ of the human body, the probabilities of occurrence of lesions related to the endoscopic image frame 450, the levels of risk of the lesions related to the endoscopic image frame 450, the levels of difficulty of identification of the lesions related to the endoscopic image frame 450, and the types of target lesions. When an organ to which the endoscopic image frame 450 is directed is specified, for example, when the endoscopic image frame 450 is related to a colonoscopy image, information about whether the image displayed in the current image frame is the beginning, middle, or end of the colonoscopy image can be identified along with a relative position in the colon (the inlet, middle, and end of the organ). Accordingly, the context-based diagnosis requirements may be extracted based on the types of lesions/diseases that are likely to occur at the identified position and region, the types of lesions/diseases that are likely to be overlooked by medical staff because they are difficult to identify with the naked eye, diagnosis information about lesions/diseases that are not easy to visually identify within the current image frame, and the types of lesions/diseases requiring attention due to their high risk/lethality during a diagnosis among the lesions/diseases that may occur at locations within the organ of the human body to which the current image frame is directed. In this case, the context-based diagnosis requirements may also include information about the types of target lesions/diseases that need to be first considered in relation to the current image frame based on the information described above.

The display information 360 may include the endoscopic image frame 450, the diagnosis results selectively overlaid on the endoscopic image frame 450, information about the diagnosis application algorithms having generated the diagnosis results, and evaluation scores for the diagnosis application algorithms. The above-described process of calculating evaluation scores in the embodiments of FIGS. 1 and 2 may be used as the process of calculating the evaluation scores for the diagnosis application algorithms.

Although priorities may be allocated to the artificial intelligence diagnosis algorithm in descending order of evaluation scores in the application of diagnoses, there are some additional factors to be taken into account.

When a first-priority artificial intelligence algorithm detects a part of the lesions that are likely to occur in connection with the corresponding endoscopic image and a subsequent-priority artificial intelligence algorithm detects an item that is not detected by the first priority algorithm, both the diagnosis results of the first-priority artificial intelligence algorithm and the diagnosis results of the subsequent-priority artificial intelligence algorithm may be displayed together. Furthermore, there may be provided a menu that allows a user to select a final diagnosis application artificial intelligence algorithm based on the above-described criteria. In order to help the user to make a selection, the menu may be displayed together with the diagnosis results of the plurality of AI algorithms and a description of the reason for displaying the diagnosis results.

For example, it is assumed that lesions A1 and A2 are known as being the types of lesions that are most likely to occur within the current image frame and a lesion B is known as being less likely to occur than lesions A1 and A2 and being likely to be overlooked because it is difficult to visually identify. An artificial intelligence diagnosis algorithm X, which has obtained the highest evaluation score for the lesions A1 and A2, may obtain the highest overall evaluation score and be selected as the first diagnosis application algorithm that is preferentially recommended. Meanwhile, there may be a case where the first diagnosis application algorithm obtains the highest evaluation score for the lesions A1 and A2 but obtains an evaluation score less than a reference value for the lesion B. In this case, the lesion B for which the first diagnosis application algorithm exhibits the performance less than the reference value may be designated as a supplemental diagnosis requirement. An artificial intelligence diagnosis algorithm Y that obtains the highest evaluation score for the lesion B, which is a supplemental diagnosis requirement, may be selected as a second diagnosis application algorithm. A combination of the first and second diagnosis application algorithms may be selected such that the combination has high evaluation scores for the reliability and accuracy of the overall diagnostic information, the diagnostic information for a specific lesion/disease is prevented from being overlooked, and the diagnostic performance for a specific lesion/disease is prevented from being poor. Accordingly, logical conditions for the selection of a diagnosis application algorithm may be designed such that an artificial intelligence diagnosis algorithm exhibiting the best performance for the supplemental diagnosis requirement for which the first diagnosis application algorithm is weak, rather than the AI reading algorithm exhibiting high overall evaluation score, is selected as the second diagnosis application algorithm.

Although the case where the two diagnosis application algorithms are selected has been described as an example in the above embodiment, an embodiment in which three or more diagnosis application algorithms are selected and applied may also be implemented according to the description given herein in the case where the combination of the three or more diagnosis application algorithms exhibits better performance according to the evaluation scores.

The embodiments of FIGS. 1 to 2 are embodiments in which the diagnosis results obtained by the application of the artificial intelligence diagnosis algorithms having high internal evaluation scores are presented and then a user may select the diagnosis results obtained by the application of artificial intelligence diagnosis algorithms having higher evaluation scores. Meanwhile, in the embodiment of FIGS. 3 and 4, there is disclosed a configuration conceived for the purpose of rapidly displaying diagnosis results for a real-time endoscopic image. Accordingly, in the embodiment of FIGS. 3 to 4, a combination of artificial intelligence diagnosis algorithms to be displayed for the current image frame is preferentially selected based on context-based diagnosis requirements, the diagnosis results of this combination are generated as display information, and the display information together with the image frame is provided to a user.

In this case, the types of lesions/diseases that are likely to occur in the current image frame, the types of lesions/diseases that are likely to occur in the current image frame and are also likely to be overlooked by medical staff because they are difficult to visually identify, and the types of lesions/diseases requiring attention during diagnosis due to their high risk/lethality among the lesions that may occur in the current image frame may be included in the context-based diagnosis requirements. Furthermore, the types of target lesions/diseases that should not be overlooked in the current image frame based on the types and characteristics of lesions/diseases, and the priorities of the types of target lesions/diseases may be included in the context-based diagnosis requirements.

When the diagnosis results and display information 360 of the present invention are used in a hospital, they are displayed by the user system 340 having a user interface capable of displaying auxiliary artificial intelligence diagnosis results after endoscopic data has been received and analyzed, and then the diagnosis results may be confirmed, the diagnosis results may be replaced, or the acceptance or rejection of the diagnosis results may be determined based on user input.

The processor 420 may store the display information 360 in the database with the display information 360 associated with the endoscopic image frame 450. In this case, the database may be a database inside the diagnosis computing system 410, and may be stored as medical records for a patient in the future.

The processor 420 may generate external storage data in which the display information 360 and the endoscopic image frame 450 are associated with each other, and may transmit the external storage data to an external database through the transmission interface module 440 so that the external storage data can be stored in the external database. In this case, the external database may be a PACS database or a database implemented based on a cloud.

In this case, the plurality of medical image diagnosis algorithms are artificial intelligence algorithms each using an artificial neural network, and the processor 420 may generate evaluation scores based on the respective diagnosis requirements/context-based diagnosis requirements as descriptive information for each of the plurality of medical image diagnosis algorithms.

The medical image diagnosis assistance method according to the other embodiment of the present invention is executed by the processor 420 in the diagnostic computing system 410 that assists a diagnosis of a medical image, and is executed based on program instructions loaded into the processor 420.

The medical image diagnosis assistance method includes: the step of receiving, by the reception interface module 430, a medical image; step 422 of extracting, by the processor 420, diagnosis requirements for the medical image by analyzing each endoscopic image frame 450 of a medical image; step 424 of selecting, by the processor 420, a plurality of diagnosis application algorithms to be applied to the diagnosis of the endoscopic image frame 450 from among a plurality of medical image diagnosis algorithms stored in a memory or database in the diagnosis computing system 410 and each having a medical image diagnosis function based on the diagnosis requirements; and step 426 of generating, by the processor 420, display information 360 including diagnosis results for the endoscopic image frame 450 by applying the plurality of selected diagnosis application algorithms to the endoscopic image frame 450.

Figure 5:
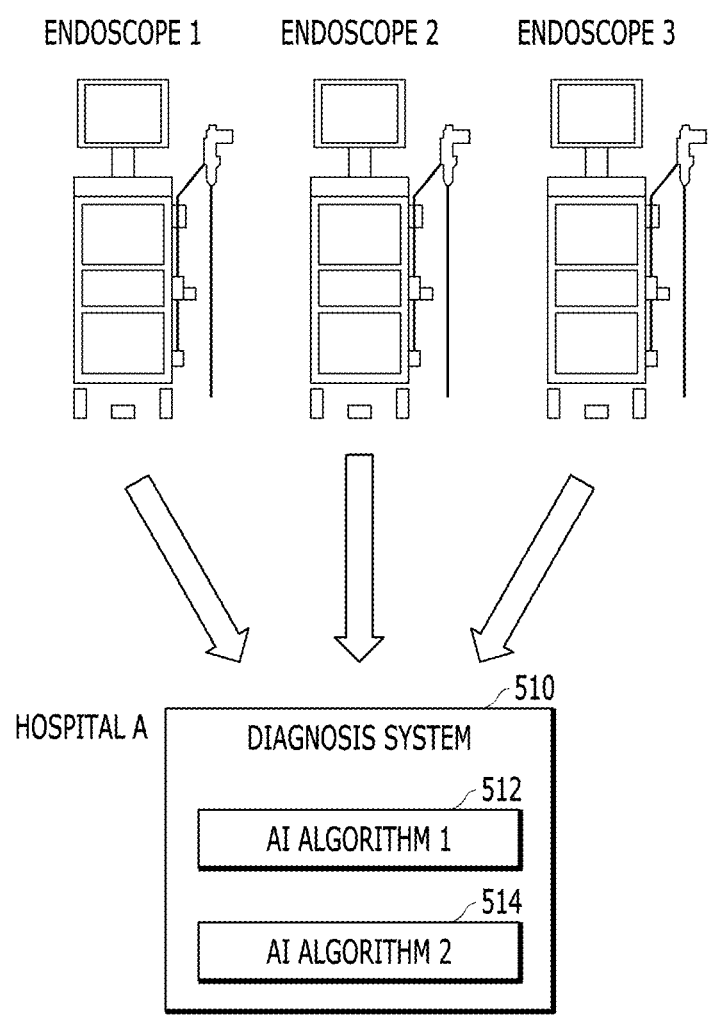
FIG. 5 is a conceptual diagram showing a workflow including a medical image diagnosis assistance apparatus according to an embodiment of the present invention.

FIG. 5 is a conceptual diagram showing a workflow including a medical image diagnosis assistance apparatus according to an embodiment of the present invention.

A diagnosis system 510 may internally include at least two artificial intelligence diagnosis algorithms 512 and 514. Endoscopic image data is transferred from three or more pieces of endoscopy equipment to the diagnosis system 510. The diagnosis system 510 generates diagnosis results by applying the at least two artificial intelligence diagnosis algorithms 512 and 514 to each frame of the endoscopic image data. The diagnosis system 510 generates display information by associating the diagnosis results with the frame of the endoscopic image data. In this case, the display information may be generated to include the identification information of a hospital (hospital A) in which the endoscopic image data is generated. Furthermore, the display information may be generated to include the identification information (endoscope 1, endoscope 2, or endoscope 3) given to each piece of endoscope equipment of each hospital.

Figure 6:
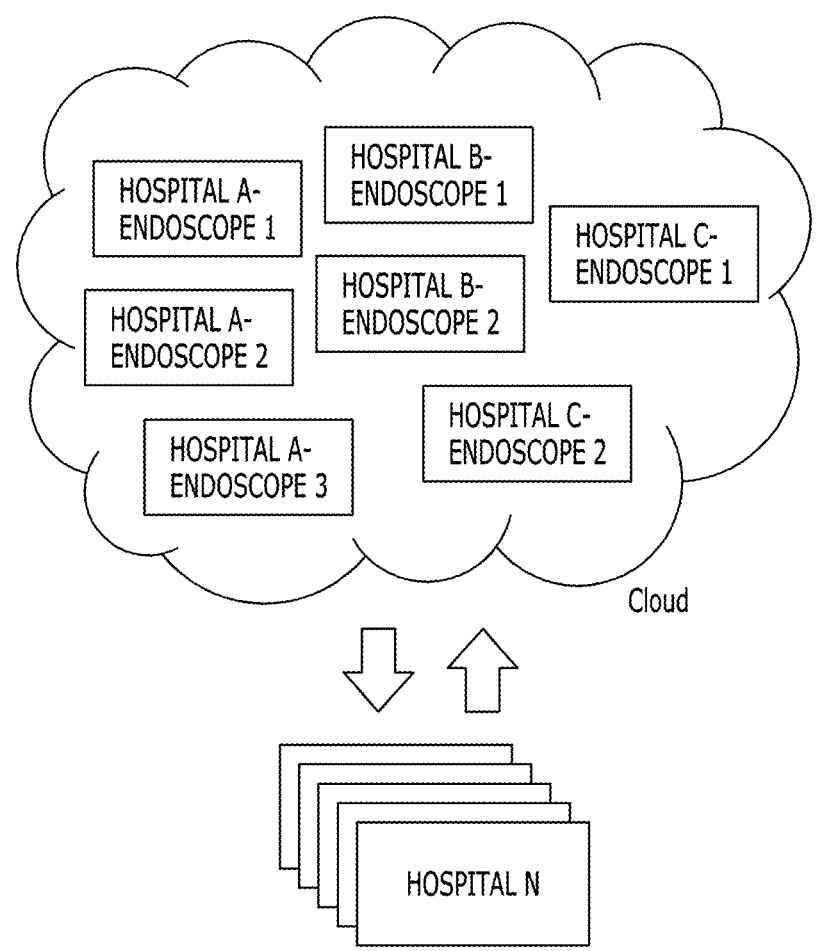
FIG. 6 is a conceptual diagram showing a workflow including a medical image diagnosis assistance apparatus according to an embodiment of the present invention.

FIG. 6 is a conceptual diagram showing a workflow including a medical image diagnosis assistance apparatus according to an embodiment of the present invention.

The diagnosis system 510 of FIG. 5 transmits the generated display information to a cloud-based database, and the endoscopic image data and the display information are stored in the cloud-based database, with the endoscopy equipment in which the endoscopic image data was generated and the hospital in which the endoscopic image data was generated being identified. The display information may be generated by associating diagnosis information with each frame of the endoscopic image data and then stored. The diagnosis information generated for each frame of the endoscopic image data may be automatically generated based on evaluation scores and context-based diagnosis requirements, as described in the embodiments of FIGS. 1 to 4.

When the present invention is applied in a cloud environment, endoscopic image data and diagnosis results may be received by a user system on a hospital side using equipment connected over a wireless communication network, and auxiliary artificial intelligence diagnosis results may be displayed on the user system.

The display information stored in the cloud database may be provided to a hospital designated by a patient, and the patient may receive his or her endoscopic image data and diagnosis information at a hospital that is convenient to access and also receive a doctor's interpretation of diagnosis results and a follow-up diagnosis at the hospital.

The method of assisting the diagnosis of a medical image according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software.

Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

According to the present invention, a user may compare the plurality of recommended diagnosis results of a plurality of artificial intelligence medical image diagnosis algorithms applicable to a corresponding image with his or her diagnosis result in the process of analyzing the medical image, thereby increasing the accuracy of the diagnosis result for the medical image by the user.

According to the present invention, a plurality of recommended diagnosis results for parts that may not be identified by a user may be compared with each other and referred to via a plurality of artificial intelligence medical image diagnosis algorithms. The user may verify his or her diagnosis result through comparison with a plurality of diagnosis results via the corresponding system, thereby achieving accurate diagnosis and increasing the confidence of diagnosis.

Furthermore, base images for a plurality of recommended diagnosis results may be referred to in the recommendation diagnosis system, so that the accuracy/confidence of the diagnosis results of a plurality of recommended artificial intelligence medical image diagnosis algorithms similar to the diagnosis result of a user may be evaluated and the user's ability to diagnose a medical image may be improved.

The evaluation of recommended artificial intelligence algorithms by a user may be linked to the charging system of an evaluation system inside the recommendation diagnosis system.

According to the present invention, evaluation scores for artificial intelligence medical image diagnosis algorithms inside the recommendation diagnosis system may be provided as descriptive information, a user may obtain information about the clinical usefulness of medical image diagnosis algorithms in the process of generating a final diagnosis result, and the information about the clinical usefulness may be fed back to the recommendation diagnosis system of the present invention.

The descriptive information that is provided by the present invention may, in turn, be beneficially used to improve the diagnosis performance of medical image diagnosis algorithms based on artificial neural networks.

According to the present invention, there may be provided the optimized content of artificial intelligence medical image diagnosis results for each real-time image frame of an endoscopic image.

According to the present invention, there may be provided the optimized content of a plurality of artificial intelligence medical image diagnosis results for each real-time image frame.

According to the present invention, there may be provided an optimized combination of a plurality of artificial intelligence medical image diagnosis results as display information for each real-time image frame.

According to the present invention, there may be provided an optimized combination of a plurality of artificial intelligence medical image diagnosis results capable of efficiently displaying diagnosis results that are likely to be diagnosed, are likely to be overlooked, or have a high level of risk in a current image frame.

According to the present invention, there may be provided the user interface and diagnosis computing system that automatically detect and present diagnosis results that are likely to be diagnosed, are likely to be overlooked, or have a high level of risk in a current image frame, so that medical staff can check and review the diagnosis results in real time during an endoscopy.

The present invention was derived from the research conducted as part of the Fundamental SW Computing Technology Development Project sponsored by the Korean Ministry of Science and ICT and the Institute for Information and Communications Technology Promotion [Project Management Number: 2018-0-00861; and Project Name: Development of Intelligent SW Technology for Analysis of Medical Data].

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A medical image diagnosis assistance apparatus for assisting a diagnosis of a medical image, the medical image diagnosis assistance apparatus comprising a computing system, wherein the computing system comprises:
   a reception interface module configured to receive an endoscopic image frame as a medical image;
   a memory or database configured to store a plurality of medical image diagnosis algorithms each having a medical image diagnosis function; and
   a processor,
   wherein the processor is configured to:
      extract diagnosis requirements for the medical image by analyzing each image frame of the medical image,
      extract a relative position indicated by the endoscopic image frame in a specified organ of a human body indicated by the endoscopic image frame as a part of the diagnosis requirements by analyzing the endoscopic image frame using an artificial neural network, wherein the relative position in the specified organ includes at least one of a beginning position, a middle position, or an end position in the specified organ;
      select a plurality of diagnosis application algorithms to be applied to a diagnosis of the image frame from among the plurality of medical image diagnosis algorithms based on the diagnosis requirements, and
      generate display information including diagnosis results for the image frame by applying the plurality of selected diagnosis application algorithms to the image frame.

2. The medical image diagnosis assistance apparatus of claim 1, wherein the processor is further configured to:
   extract context-based diagnosis requirements corresponding to characteristics of the image frame of the medical image by analyzing the image frame of the medical image; and
   select a plurality of diagnosis application algorithms to be applied to the diagnosis of the image frame based on the context-based diagnosis requirements.

3. The medical image diagnosis assistance apparatus of claim 2, wherein the processor is further configured to:
   select a combination of the plurality of diagnosis application algorithms based on the context-based diagnosis requirements; and
   generate display information including diagnosis results for the image frame by applying the combination of the plurality of diagnosis application algorithms to the image frame.

4. The medical image diagnosis assistance apparatus of claim 3, wherein the combination of the plurality of diagnosis application algorithms comprises:
   a first diagnosis application algorithm configured to be preferentially recommended for the image frame based on the context-based diagnosis requirements; and a second diagnosis application algorithm configured to be recommended based on a supplemental diagnosis requirement derived from the context substrate diagnosis requirements based on a characteristic of the first diagnosis application algorithm.

5. The medical image diagnosis assistance apparatus of claim 2, wherein the context-based diagnosis requirements comprise one or more of a body part of the human body included in the endoscopic image frame, the organ of the human body, the relative position indicated by the endoscopic image frame in the organ of the human body, probabilities of occurrence of lesions related to the endoscopic image frame, levels of risk of the lesions related to the endoscopic image frame, levels of difficulty of identification of the lesions related to the endoscopic image frame, or types of target lesions.

6. The medical image diagnosis assistance apparatus of claim 1, wherein the display information comprises the image frame, the diagnosis results selectively overlaid on the image frame, information about the diagnosis application algorithms having generated the diagnosis results, and evaluation scores for the diagnosis application algorithms.

7. The medical image diagnosis assistance apparatus of claim 1, wherein the processor is further configured to store the display information in the database with the display information associated with the image frame.

8. The medical image diagnosis assistance apparatus of claim 1, wherein the processor is further configured to:
generate external storage data in which the display information is associated with the image frame; and
transmit the external storage data to an external database through a transmission interface module so that the external storage data is stored in the external database.

9. A medical image diagnosis assistance method, the medical image diagnosis assistance method being executed by a processor inside a computing system for assisting a diagnosis of a medical image, the medical image diagnosis assistance method being executed based on program instructions loaded into the processor, the medical image diagnosis assistance method comprising:
receiving, by a reception interface module, an endoscopic image frame as a medical image;
extracting, by the processor, diagnosis requirements for the medical image by analyzing each endoscopic image frame of a medical image, wherein the extracting further comprises extracting, by the processor, a relative position indicated by the endoscopic image frame in awa specified organ of a human body indicated by the endoscopic image frame as a part of the diagnosis requirements by analyzing the endoscopic image frame using an artificial neural network, wherein the relative position in the specified organ includes at least one of a beginning position, a middle position, or an end position in the specified organ;
selecting, by the processor, a plurality of diagnosis application algorithms to be applied to a diagnosis of the image frame from among a plurality of medical image diagnosis algorithms stored in a memory or database inside the computing system and each having a medical image diagnosis function based on the diagnosis requirements; and
generating, by the processor, display information including diagnosis results for the image frame by applying the plurality of selected diagnosis application algorithms to the image frame.

10. The medical image diagnosis assistance method of claim 9, wherein the extracting comprises extracting, by the processor, context-based diagnosis requirements corresponding to characteristics of the image frame of the medical image by analyzing the image frame of the medical image, and
wherein the selecting comprises selecting, by the processor, a plurality of diagnosis application algorithms to be applied to the diagnosis of the image frame based on the context-based diagnosis requirements.

11. The medical image diagnosis assistance method of claim 10, wherein the selecting comprises selecting, by the processor, a combination of the plurality of diagnosis application algorithms, including a first diagnosis application algorithm configured to be preferentially recommended for the image frame based on the context-based diagnosis requirements and a second diagnosis application algorithm configured to be recommended based on a supplemental diagnosis requirement derived from the context substrate diagnosis requirements based on a characteristic of the first diagnosis application algorithm, based on the context-based diagnosis requirements, and
wherein the generating comprises generating, by the processor, display information including diagnosis results for the image frame by applying the combination of the plurality of diagnosis application algorithms to the image frame.

12. The medical image diagnosis assistance method of claim 9, further comprising:
storing, by the processor, the display information in the database with the display information associated with the image frame.

13. The medical image diagnosis assistance method of claim 9, further comprising:
generating, by the processor, external storage data in which the display information is associated with the image frame; and
transmitting, by the processor, the external storage data to an external database through a transmission interface module so that the external storage data is stored in the external database.

* * * * *